(12) United States Patent
Alcantara et al.

(10) Patent No.: US 7,070,672 B2
(45) Date of Patent: Jul. 4, 2006

(54) PROCESS FOR MAKING A FEMININE SANITARY NAPKIN OR OTHER ABSORBENT ARTICLE HAVING PLACE AND CUT WINGS

(75) Inventors: Glory Framary Alcantara, Neenah, WI (US); David Joseph Nickel, Menasha, WI (US); Arthur Wesley Leiphart, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 165 days.

(21) Appl. No.: 10/785,869

(22) Filed: Feb. 24, 2004

(65) Prior Publication Data

US 2005/0183814 A1  Aug. 25, 2005

(51) Int. Cl.
*B32B 37/00* (2006.01)
*A61F 13/15* (2006.01)

(52) U.S. Cl. ............... 156/265; 156/269; 156/301; 156/302; 156/512; 156/519; 156/522

(58) Field of Classification Search ............... 156/253, 156/265, 269, 302, 519, 522, 552, 518, 520, 156/301; 604/385.04
See application file for complete search history.

(56) References Cited

U.S. PATENT DOCUMENTS

| | | | |
|---|---|---|---|
| 4,900,320 A * | 2/1990 | McCoy | 604/387 |
| 5,584,954 A | 12/1996 | Van der Klugt | |
| 5,660,665 A | 8/1997 | Jalonen | |
| 5,858,515 A | 1/1999 | Stokes et al. | |
| 6,465,711 B1 | 10/2002 | Brisebois | |
| 6,659,991 B1 * | 12/2003 | Suekane | 604/385.04 |

| | | |
|---|---|---|
| 2002/0068917 A1 | 6/2002 | Vangompel et al. |
| 2002/0156445 A1 | 10/2002 | Suekane |

FOREIGN PATENT DOCUMENTS

| | | |
|---|---|---|
| DE | 42 26 739 A1 | 2/1994 |
| EP | 1 062 928 A1 | 12/2000 |
| WO | WO 93/06805 A1 | 4/1993 |
| WO | WO 99/65439 A1 | 12/1999 |
| WO | WO 01/00122 A1 | 1/2001 |
| WO | WO 2002/083047 A1 | 10/2002 |

OTHER PUBLICATIONS

INDA Standard Test Method IST 70.4 (99), "Standard Test Method for Water Vapor Transmission Rate Through Non Woven and Plastic Film Using a Guard Film and Vapor Pressure Sensor," Copyright 1995, 7 pages.

* cited by examiner

*Primary Examiner*—Linda Gray
(74) *Attorney, Agent, or Firm*—Paul Yee

(57) ABSTRACT

A process (100) for forming an article (20) includes delivering an article web (120) which provides an interconnected plurality of article-segments (104). At least one selected article-segment (104) can include at least one wing-panel component or member (142), which has been operatively joined to its corresponding, selected article-segment (104) and configured to extend beyond at least one laterally-opposed side edge of said article web (120) in an intermediate portion (76) of the corresponding article-segment (104). The process (100) can also include a substantially continuous severing of the article web (120) and the at least one wing-panel member (142) to provide a contoured composite web. The contoured composite web can include at least one contoured wing-panel (142). In addition, a contoured side-edge (64) of the contoured wing-panel (142) can be configured to extend substantially continuously from a cooperatively contoured side-edge (74) of the article web.

20 Claims, 8 Drawing Sheets

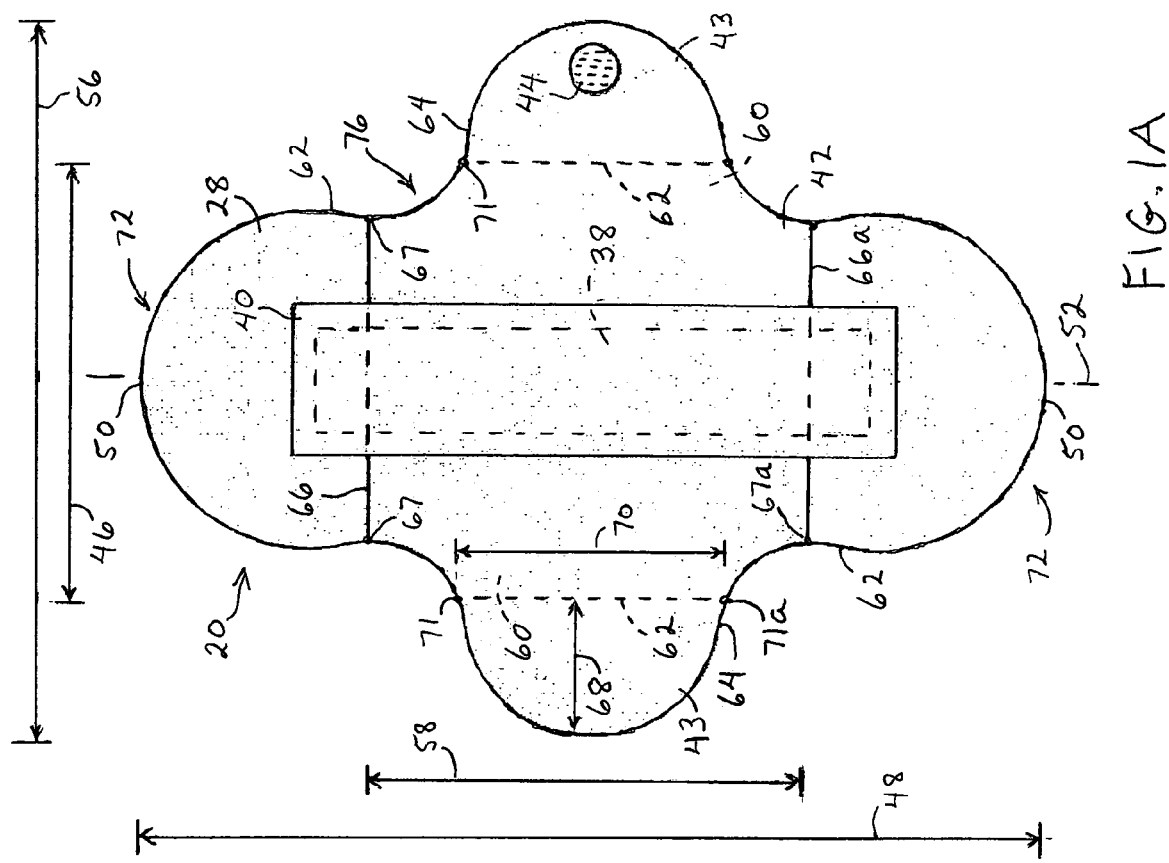
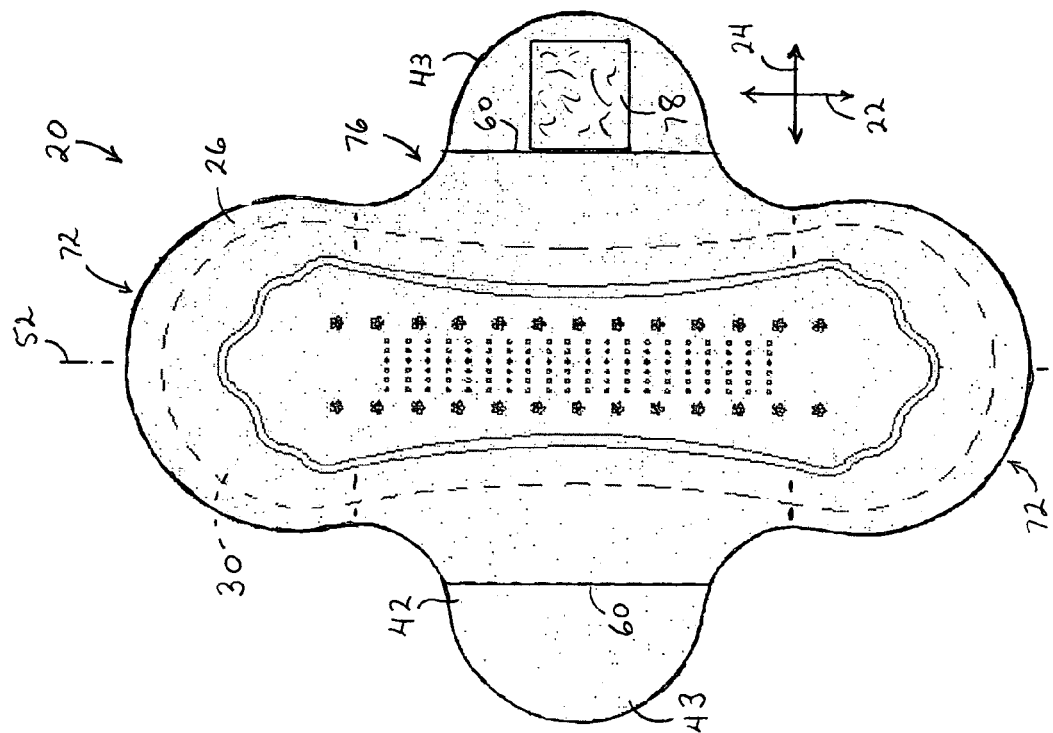

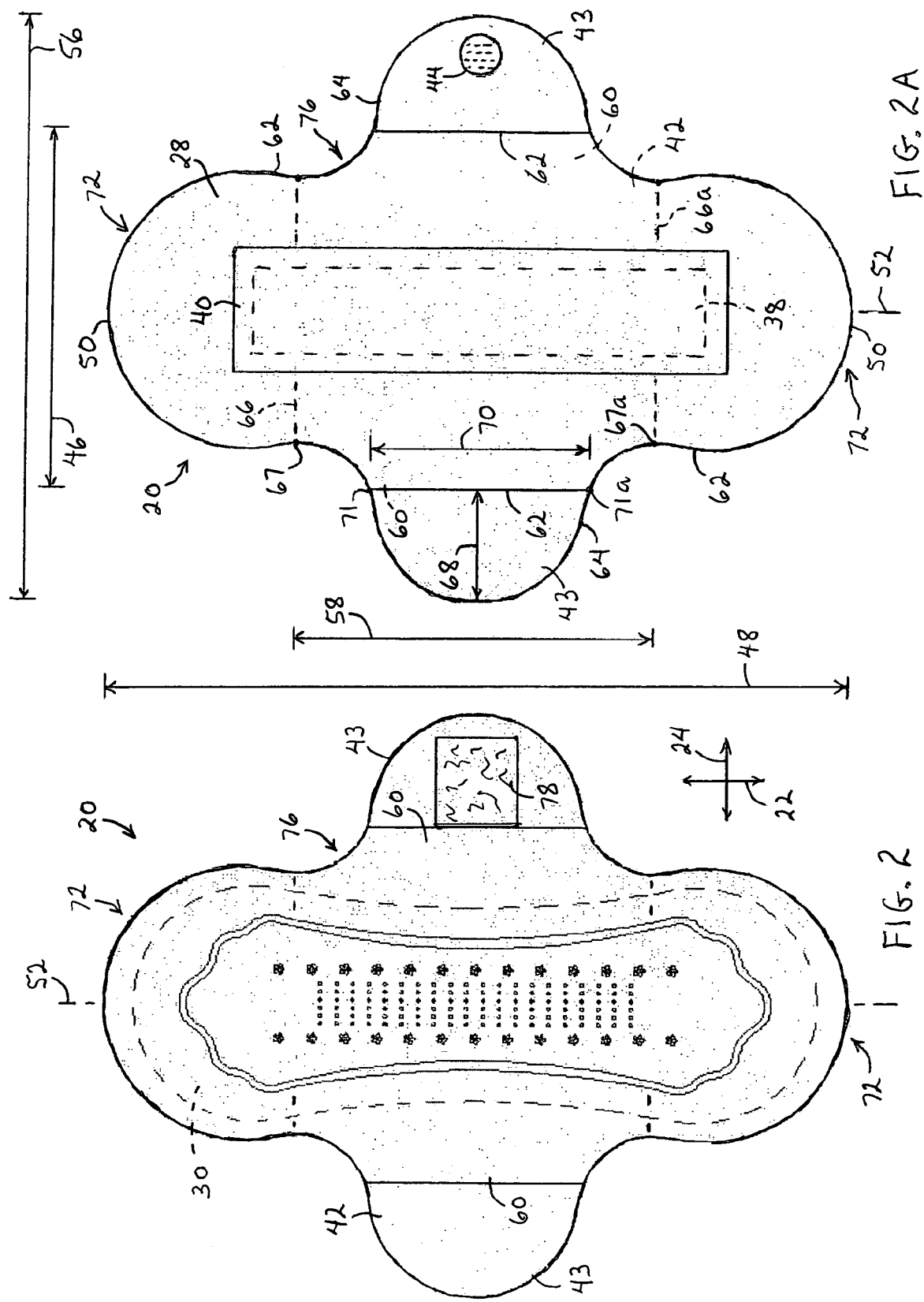

PROCESS FOR MAKING A FEMININE SANITARY NAPKIN OR OTHER ABSORBENT ARTICLE HAVING PLACE AND CUT WINGS

FIELD OF THE INVENTION

The present invention relates to a fastening system for an absorbent article. More particularly, the present invention pertains to a feminine care article, such as a feminine care pad, having a system of one or more wing-panels.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that, feminine care articles have been employed to absorb and hold liquids, such as urine and/or menses. In particular arrangements, the feminine care articles have included wing portions which can help to hold the article in place at a selected location in a wearer's undergarment. In some arrangements, the wing portions have been integrally formed with one or more of the preexisting component layers that were employed to construct the article. In other arrangements, the wing portions have been separately provided components that are assembled and affixed to the final product. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent articles with wing portions, however, have not provided desired combinations of securement, comfort, performance and versatility. When conventional articles have been constructed with integrally formed wing components, it has been difficult to provide the wing portions with desired, differentiated characteristics. When conventional articles have been constructed with separately provided wing components, the finished product has not provided sufficient levels of aesthetic appeal and attractiveness. As a result, there has been a continued need for an improved article design that provides the attractiveness and aesthetic appeal afforded by integrally formed wing portions, and also affords the versatility and enhanced performance that can arise from separately provided wing portions that are constructed from different materials having selected characteristics and performance parameters.

BRIEF DESCRIPTION OF THE INVENTION

Generally stated, the method of the present invention provides a distinctive process for forming an article, such as an absorbent article. The process includes delivering an article web, which has a longitudinal-direction and a lateral cross-direction. The article web provides an interconnected plurality of article-segments, and each article-segment includes an intermediate portion located between a pair of longitudinally-opposed end portions. At least one selected article-segment can include at least one wing-panel, which has been operatively joined to its corresponding, selected article-segment and configured to extend beyond at least one laterally-opposed side edge of said article web in the intermediate portion of the corresponding article-segment. The process can also include a substantially continuous severing the article web and the at least one wing-panel to provide a contoured composite web. At the selected article-segment, a contoured side-edge of the wing-panel extends substantially continuously from a cooperatively contoured side-edge of said article web. Desirably, the wing-panel can be configured to be wrapped about a side edge of a wearer's undergarment.

By incorporating its various features and configurations, the method of the invention can provide an article having the attractiveness and aesthetic appeal afforded by integrally formed wing portions, while also providing the versatility and enhanced performance that can arise from incorporating separately provided wing portions that are constructed from different materials having selected characteristics and performance parameters. The article can be more efficiently manufactured at high speed and with lower costs.

BRIEF DESCRIPTION OF THE DRAWINGS

The various features, aspects and advantages of the present invention will become better understood with reference to the following description, appended claims and accompanying drawings where:

FIG. 1 shows a top, plan view of a bodyside of a representative feminine care article in which side portions of at least one wing-panel are arranged in a laterally-extended position and the wing panel is positioned adjacent an outside surface of the article.

FIG. 1A shows a bottom, plan view of a garment-side of the representative feminine care article illustrated in FIG. 1.

FIG. 2 shows a top, plan view of a bodyside of another representative feminine care article in which side portions of a singular wing-panel are arranged in a laterally-extended position and the wing panel is positioned adjacent an inside surface of the article.

FIG. 2A shows a bottom, plan view of a garment-side of the representative feminine care illustrated in FIG. 2.

DETAILED DESCRIPTION OF THE INVENTION

Figure 3:
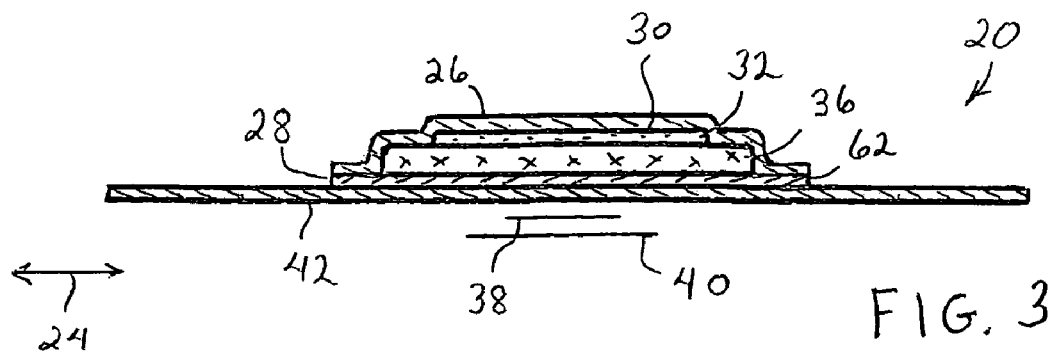
FIG. 3 shows a partially-expanded view of a representative lateral, transverse cross-section through an article having a singular wing-panel positioned against a garment-side surface of a backsheet of the article.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the adsorbent material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof, can operate to provide a body-facing surface and a garment-facing surface. As used herein, "body-facing surface" means that surface of the article or component which is intended to be disposed toward or placed adjacent to the body of the wearer during ordinary use, while the "outward surface" or "outward-facing surface" is on the opposite side, and is intended to be disposed to face away from the wearer's body during ordinary use. The outward surface may be arranged to face toward or placed adjacent to the wearer's undergarments when the absorbent article is worn.

FIGS. 1 through 5C illustrate examples of a suitable article 20, such as the representatively shown feminine care article, which is configured to incorporate the present invention. The feminine care article can, for example, be a feminine care pad or napkin, and the article can have a lengthwise longitudinal direction 22, a transverse, laterally extending, cross-direction 24, first and second longitudinally opposed end portions 72, and an intermediate portion 76 located between the end portions. As representatively shown, the longitudinal dimension of the article is relatively larger than the lateral dimension of the article. The article 20 can include a baffle or backsheet 28, a liquid-permeable cover or topsheet 26, and an absorbent structure 30 which is operatively positioned and sandwiched between the backsheet 28 and topsheet 26. As representatively shown, peripheries of the topsheet and backsheet may be substantially entirely coterminous. Alternatively, the peripheries of the topsheet 26 and the backsheet 28 may be partially or entirely non-coterminous. At least one wing-panel member 42 can be operatively joined to the intermediate portion 76 of the article 20. In particular aspects of the article, the wing-panel can extend laterally beyond at least one lateral side edge of either or both of the topsheet 26 and backsheet 28 in the article intermediate portion 76, and the wing-panel 42 can be configured to wrap about an undergarment, particularly a crotch section of the undergarment.

In a particular feature, a maximum longitudinal length 58 of the wing panel 42 can be less than a maximum longitudinal length 48 of the backsheet 28. In another feature, a contoured side-edge 64 of the wing-panel 42 can provide a substantially continuous extension from a contoured side-edge 62 of the topsheet 26 and/or backsheet 28. A further feature can include a singular wing-panel that is positioned and configured to extend transversely beyond a laterally opposed pair of side edges of the topsheet and/or backsheet 28. Optionally, a cooperating plurality of wing-panels 42 can be operatively joined to the article intermediate portion 76, and each of the wing-panels can be configured to extend transversely beyond a corresponding side edge of the backsheet 28.

By incorporating its various aspects, features and configurations (alone or in desired combinations), the article of the invention can provide the attractiveness and aesthetic appeal afforded by integrally formed wing portions, while also providing the versatility and enhanced performance that can arise from incorporating separately provided wing portions that are constructed from different materials having selected characteristics and performance parameters.

The cover or topsheet 26 may include any material that can be configured to provide the topsheet with an operative level of liquid-permeability. The topsheet may be constructed with one or more layers of suitable materials, and may be a composite material. For example, the topsheet layer can include a woven fabric, a nonwoven fabric, a polymer film, a film-fabric laminate or the like, as well as combinations thereof. Examples of a nonwoven fabric include, spunbond fabric, meltblown fabric, coform fabric, a carded web, a bonded-carded-web, a bicomponent spunbond fabric or the like as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable topsheet layer material can include a bonded-carded-web composed of polypropylene and polyethylene, such as has been used as a topsheet stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the topsheet layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. The topsheet layer 26 can provide comfort and conformability, and can function to direct bodily exudates away from the body and toward the absorbent structure 30. In a desired feature, the topsheet layer 26 can be configured to retain little or no liquid in its structure, and can be configured to provide a relatively comfortable and non-irritating surface next to the body-tissues of a female wearer. The topsheet layer 26 can be constructed of any material which is also easily penetrated by bodily fluids that contact the surface of the topsheet layer.

The topsheet 26 can also have at least a portion of its bodyside surface treated with a surfactant to render the topsheet more hydrophilic. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

The topsheet 26 may be maintained in secured relation with the absorbent structure 30 by bonding all or a portion of the adjacent surfaces to one another. A variety of bonding techniques known to one of skill in the art may be utilized to achieve any such secured relation. Examples of such techniques include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the absorbent.

The topsheet 26 typically extends over the upper, bodyside surface of the absorbent structure to provide a bodyside liner, but can alternatively extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins can be joined together to partially or entirely, surround or enclose the absorbent structure.

The baffle or backsheet 28 may include a layer constructed of any operative material, and may or may not be configured to be liquid-permeable. In a particular configuration, the cover or backsheet 28 may be configured to provide an operatively liquid-impermeable layer. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable backsheet available from Hanjin Printing, Hanjin P&C Company Limited, a business having offices located in Sahvon-li.Junganmvu.Kongiu-City, Chung cheong nam-do, Republic of South Korea. The backsheet material is a breathable film, which is white in color, dimple embossed, and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber.

The absorbent structure 30 may also include superabsorbent material. Superabsorbent materials suitable for use in the present invention are known to those skilled in the art, and may be in any operative form, such as particulate form. Generally stated, the water-swellable, generally water-insoluble, hydrogel-forming polymeric absorbent material (superabsorbent) is capable of absorbing at least about 10, desirably about 20, and possibly about 100 times or more its weight in water. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company, Hoechst Celanese Corporation, Allied Colloid Inc., and Stockhausen, Inc.

The absorbent body 30 can be substantially unitary with a non-uniform structure or a generally uniform structure. Alternatively, the absorbent body may include a composite structure having a selected plurality of strata or layers. For example, the absorbent body structure may include an intake layer, a distribution layer, a transfer layer, a transfer-delay layer, a shaping layer, a retention layer or the like, as well as combinations thereof. The various strata and/or layers may be layered or otherwise arranged in any operative sequence or configuration.

Additionally, the absorbent article can include any desired pattern or array of embossments. In particular aspects, the embossments may be formed on the bodyside surface of the article. Desired arrangements can include an absorbent body structure that has embossment regions formed on at least its bodyside surface. Similarly, the other employed components of the article can also include corresponding embossed regions.

With reference to FIGS. 3 through 3C and FIGS. 5 through 5C, the absorbent composite may, for example, include either or both of an intake layer 32, and an absorbent retention layer 36. As representatively shown, the absorbent body can include an absorbent retention layer 36 which is positioned between the topsheet 26 and the backsheet 28. Additionally, the absorbent body can include an intake layer 32 which is positioned between topsheet 26 and the pad retention layer 36. The absorbent body can further include one or more additional layers positioned between the topsheet 26 and backsheet 28. The various individual layers may be separately provided layer-components, may be integrally formed together, or may be provided as any operative combination of separately-provided and integrally-formed layers.

The intake layer 32 can provide a desired intake of liquid and distribution of the liquid. The intake layer may include natural fibers (e.g. cellulose fibers), synthetic fibers, superabsorbent materials, a woven fabric; a nonwoven fabric; a wet-laid fibrous web; a substantially unbonded airlaid fibrous web; an operatively bonded, stabilized-airlaid fibrous web; a multifunctional stabilized-airlaid fibrous web; or the like, as well as combinations thereof.

In a particular arrangement, the intake layer can be a thermally-bonded, stabilized-airlaid fibrous web having a basis weight of about 175–200 g/m$^2$, and a density of about 0.06–0.08 grams/cm$^3$. Suitable stabilized-airlaid webs are available from Concert Fabrication, a business having offices located in Gatineaux, Quebec, Canada.

The retention layer 36 can provide a desired, absorbent retention or storage function, and may provide a selected shaping of the absorbent article. The retention layer may include natural fibers (e.g. cellulose fibers), synthetic fibers, superabsorbent materials, a woven fabric; a nonwoven fabric; a wet-laid fibrous web; a substantially unbonded airlaid fibrous web; an operatively bonded, stabilized-airlaid fibrous web; a multifunctional stabilized-airlaid fibrous web; or the like, as well as combinations thereof.

In desired configurations, the absorbent body 30 can provide an overall, total absorbent capacity which is at least a minimum of about 10 grams of menses simulant. The overall absorbent capacity can alternatively be at least about 20 grams of menses simulant, and can optionally be at least about 30 grams of menses simulant to provide improved performance. In other aspects, the overall absorbent capacity can be up to a maximum of about 120 grams of menses simulant, or more. The overall absorbent capacity can alternatively be up to about 100 grams of menses simulant, and can optionally be up to about 90 grams of menses simulant to provide improved effectiveness.

In a representative example, the article can include a nonwoven spunbond topsheet having a basis weight of about 20.3 g/m$^2$, and treated with 0.3% AHCOVEL surfactant. The AHCOVEL surfactant acts as a wetting agent to promote liquid intake. The intake layer of the article can comprise a generally homogeneous, stabilized-airlaid fibrous web having a basis weight of about 250 g/m$^2$, and a density of about 0.14 g/cm$^3$. The transfer layer can include a rose colored 27.1 g/m$^2$ spunbond nonwoven fabric treated with 0.3% AHCOVEL surfactant. The transfer layer can help to regulate liquid transfer from the intake layer to the retention layer. The retention layer can be a generally homogeneous, stabilized-airlaid fibrous web having a density of about 0.08 g/cm$^3$ and a basis weight of about 175 g/m$^2$. The backsheet can be a 0.7 mil (0.018 mm) thick, micro-embossed, polypropylene film, which can substantially prevent liquid from reaching the undergarment and can act as the substrate for the absorbent structure.

With reference to FIGS. 1–1A, FIGS. 2–2A, and FIGS. 4–4A, a selected configuration of a garment-fastener mechanism may be operatively distributed and joined onto the garment-side of the article 20 to help secure the article to the undergarment. The garment-fastener can include any operative fastener mechanism, such as a component of an interengaging mechanical fastener, an adhesive fastener, a cohesive fastener, a magnetic fastener, and electromechanical fastener or the like, as well as combinations thereof. For example, the garment-fastener be provided by the representatively shown adhesive 38, and the adhesive may be arranged in the illustrated strip regions that are distributed onto the garment-side of the article. Typically, the garment adhesive can be distributed over the garment-side of the backsheet, and one or more layers or sheets of release material 40 can be removably placed over the garment adhesive during storage prior to use.

The article 20 can include a system of one or more wing-panel portions 42 positioned along either or both lateral sides of the article. The wing-panels may be integrally formed from another component of the article, such as the topsheet and/or the backsheet, and operatively connected to appointed sections of the article side regions 60 along the intermediate portion of the article. Desirably, the wing-panels or wings can be separately provided members that are subsequently attached or otherwise joined to the intermediate portion of the article 20.

The wing-panels can have an appointed storage position in which the wing-panels 42 are directed generally inwardly toward the longitudinally-extending centerline 52. The wing-panel that is connected to extend from one side margin may have sufficient cross-directional length to extend and continue past the centerline 52 to approach the laterally opposite side margin of the article. The storage position of the wing-panels can ordinarily represent an arrangement observed when article is first removed from its wrapper or other packaging. Prior to placing the article into a bodyside of an undergarment prior to use, the wing-panels 42 can be selectively arranged to extend laterally from the side regions 60 of the article intermediate portion. After placing the article in the undergarment, the wing-panels 42 can be operatively wrapped and secured around the side edges of the undergarment crotch portion to help hold the article in place, in a well known, conventional manner.

The wing-panel portions 42 can have any operative construction, and can include a layer of any operative material. Additionally, each wing-panel can comprise a laminate or other composite material. For example, the wing-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Figures 4, 4A:
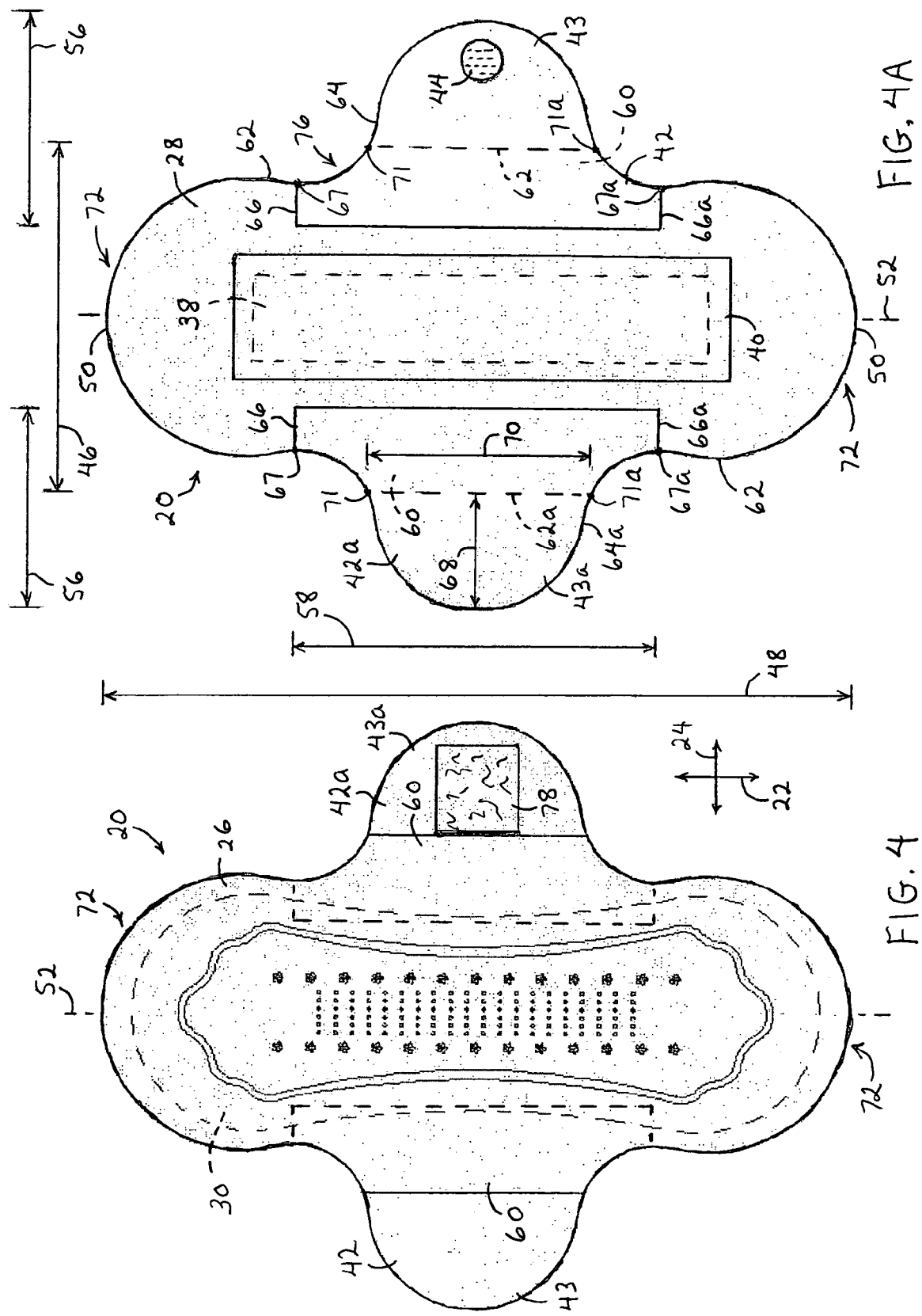
FIG. 4 representatively shows a top plan view of the bodyside of another representative feminine care article in which a plurality of separately provided wing-panel portions are arranged in a laterally-extended position.
FIG. 4A shows a bottom, plan view of a garment-side of the representative feminine care article illustrated in FIG. 4.

With reference to FIGS. 1A, 2A and 4A, the wing-panel 42 can have a transverse-length 56 and a longitudinal-length 58. In desired configurations, a maximum longitudinal-length 58 of the wing panel 42 can be less than a maximum longitudinal length of the article 20. For example, the maximum longitudinal length of the wing-panel 42 can be less than a maximum longitudinal length 48 of the backsheet 28. In a particular feature, the overall longitudinal-length of the wing-panel 42 can be up to about 80% of an overall longitudinal-length 48 of the backsheet 28. The overall longitudinal-length 58 of the wing-panel 42 can alternatively be up to about 60% of the overall longitudinal-length of the backsheet, and can optionally be up to about 50% of the overall longitudinal-length 48 of the backsheet 28 to provide improved benefits. In another aspect, the overall longitudinal-length 58 of the wing-panel 42 can be not less than a minimum of about 15% of an overall longitudinal-length 48 of the backsheet 28. The overall longitudinal-length of the wing-panel can be not less than a minimum of about 25% of an overall longitudinal-length 48 of the backsheet 28, and can optionally be not less than a minimum of about 45% of an overall longitudinal-length 48 of the backsheet 28 to provide improved performance. Additionally, longitudinally opposed end-edges 66 of the wing-panel 42 are non-coterminous with the longitudinal end-edges 50 of the backsheet 28.

As representatively shown, at least one outboard wing-section 43 of the wing-panel 42, can extend beyond each of the laterally-opposed side-edges of the topsheet 26 and/or backsheet 28 along a wing-section distance 68. In a particular arrangement, the wing-panel 42 can extend beyond the laterally-opposed side-edges 62 of the backsheet 28 over the selected wing-section distance 68. As representatively shown, a transversely-opposed pair of cooperating wing-sections 43 can be configured to extend laterally outboard from the transversely-opposed side edges of the topsheet and/or backsheet. The transversely-opposed pair of cooperating wing-sections can be substantially aligned along the cross-direction 24, and can be substantially mirror-images of each other. In particular aspects, the wing-section distance can be at least a minimum of about 2 centimeters (cm). The wing-section distance 68 can alternatively be at least about 3 cm, and can optionally be at least about 4 cm to provide improved performance. In other aspects, the wing-section distance 68 can be up to a maximum of about 10 cm, or more. The wing-section distance can alternatively be up to about 7 cm, and can optionally be up to about 5 cm to provide improved effectiveness.

If the transverse-length and/or the longitudinal-length of the wing panel is outside the desired values, various problems can occur. Overly large wing-panels may cause excessive waste and poor processing. Overly small wing panels can cause poor securement of the article to the wearer's undergarment.

The contoured side-edge 64 of the wing-panel 42 can provide a substantially continuous extension from the contoured side-edge of the topsheet 26 and/or backsheet 28. As representatively shown, the contoured side-edge 64 of the wing-panel 42 can form and provide a substantially continuous extension from the contoured side-edge 62 of the backsheet 28, and can also form and provide a substantially continuous extension from a corresponding, contoured side-edge of the topsheet 26. The structure of the substantially continuous extension can provide a combined, side-edge contour of the article which is substantially smooth and uninterrupted at the location where the terminal side edge of the material of the wing-panel 42 intersects the terminal side edge of the material of the topsheet and/or backsheet 28. Accordingly, as discerned by the ordinary, unaided human eye at a distance of 18 inch (46 cm) with no added magnification, there is substantially no discrete angular break in the line of the article side-edge contour as one progresses from the contoured side-edge 62 of the backsheet 28 onto the contoured side-edge 64 of the wing panel 42.

In a particular feature of the article 20, the backsheet 28 and the wing-panels 42 and/or 42a have been severed in a substantially continuous operation which has occurred after the wing-panels have been operatively joined to the intermediate portion 76 of the article 20. Additionally, the topsheet 26 and the wing-panels can be severed in a substantially continuous operation which has occurred after the wing-panels have been operatively joined to the article intermediate portion. The severing can occur along either or both of the laterally-opposed side regions of the article, and can be configured to produce the desired, final shape of the contours along the lateral side regions of each article. In particular arrangements, at least a significant portion of the severing of the backsheet and wing-panel can be conducted with a substantially simultaneous operation, and the severing can produce the desired, final shape of the edge contour along each lateral side region of the backsheet 28 and along each corresponding wing-panel 42.

The wing-panel 42 can have an intermediate length 70 which extends longitudinally between a pair of intersect, end-points 71 and 71a where the terminal, outline edge of an individual wing-section 43 crosses its corresponding longitudinally-extending, terminal side-edge of the backsheet 28. With respect to an individual side margin 60 of the article, the inboard boundary portion of the corresponding wing-section 43 can intersect the corresponding terminal side edge of the backsheet 28 along the intermediate length 70 to provide a base region of the wing-section. In a particular aspect, the intermediate length 70 can be smaller than the overall longitudinal-length 58 of the wing-panel.

Each wing-panel 42 can have a longitudinally-opposed pair of terminal end-edges 66 and 66a. With respect to an individual side margin 60 of the article, the end-edges 66 and 66a can each intersect the corresponding side-edge of the backsheet 28 at their corresponding intersect-points 67 and 67a, respectively. With regard to the various configurations of the article 20, the intersect-points 71, 71a, 67 and 67a are also potentially present. In a particular aspect, at least two of the intersect-points are present and readily discernable along the selected, individual side margin 60. In another aspect, at least three of the intersect-points can be present and separately discernable along the selected, individual side margin. A further aspect can include a configuration in which all four of the intersect-points that are present and separately discernable along the selected, individual side margin 60.

With regard to a pair of proximately adjacent, intersect-points (e.g. intersect-points 71 and 67) that may be provided by an individual wing-panel 42 in the article 20, a composite transition section of the terminal side edge of the article can extend between the adjacent intersect-points. In a particular aspect, the composite transition section can be arcuate or otherwise nonlinear. In another aspect, the composite transition section can extend substantially continuously with substantially no abrupt angular breaks or discontinuities. At least a significant portion of the composite transition section is nonparallel to both the longitudinal and lateral directions of the article.

Along the composite transition section, a portion of the wing-panel 42 is present, along with a portion of the article that includes a corresponding portion of the backsheet 28 and/or topsheet 26. As representatively shown, the corresponding portions of the backsheet and topsheet can be arranged and attached in a laminated or otherwise layered configuration with respect to their associated portion of the wing-panel. Additionally, the wing-panel 42 can be substantially coterminous with the backsheet 28 and/or topsheet 26 along the composite transition section.

In a particular aspect, the composite transition section can include a portion of the wing-panel member that has been substantially simultaneously severed along with a corresponding portion of the backsheet and or topsheet. As representatively shown, the composite transition section can be configured to be arcuate and concave-outward. Other arrangements, shapes and alignments may optionally be employed. A particular aspect of the article can include at least one arcuate section along at least one individual article side margin 60. In another aspect, the article can include two arcuate sections along an individual article side margin, and the first arcuate section can be arranged in an approximately mirror-image configuration relative to the second arcuate section. Still another aspect can include at least one arcuate section along each of the laterally-opposed pair of article side margins 60. A desired arrangement can include two arcuate sections along each of the two article side margins.

The contoured wing-panel 42, and particularly the contoured wing-sections 43, can be provided with any operative shape. As representatively shown, the contoured shape of the wing-panel can have a curvilinear outline. Alternatively, the outline shape can include linear sections, rectilinear sections, polygonal sections, nonlinear sections, curvilinear sections or the like, as well as combinations thereof. Curved sections can be concave or convex, and may have constant or non-constant radii of curvature.

In the various configurations of the invention, the wing panel 42 can be a separately provided component and can be joined to a major facing-surface of the article. In a particular arrangement, the wing panel 42 can be joined to a major facing-surface of the backsheet 28. In particular arrangements, the backsheet 28 can have a backsheet intermediate section interposed between a pair of longitudinally opposed, backsheet end sections, and the wing-panel 42 can be operatively joined in a configuration which can be arranged to operatively extend laterally from the intermediate section of the backsheet 28. The wing-panel may be directly or indirectly joined to the backsheet, as desired.

With reference to FIGS. 1 through 3C, at least an operative portion of an individual, singular wing-panel 42 can extend substantially continuously along an entire cross-directional width of a corresponding region of the topsheet 26 and/or backsheet 28. In particular features, the wing-panel can have a contiguous substantially unitary structure, and at least a significant portion of a medial section of the wing-panel 42 can be arranged to extend along and across an entire cross-directional width of the corresponding region(s) of either or both of the topsheet and backsheet. At least a significant portion of the medial section of the wing-panel 42 can also be arranged to extend along and across an entire cross-directional width of the corresponding region of the absorbent body 30. Additionally, a pair of distal laterally-opposed side portions 43 of the wing-panel 42 can extend from lateral sides of the wing-panel medial section, and can extend laterally beyond the pair of laterally-opposed, terminal side edges of the backsheet and/or topsheet.

Figure 3A:
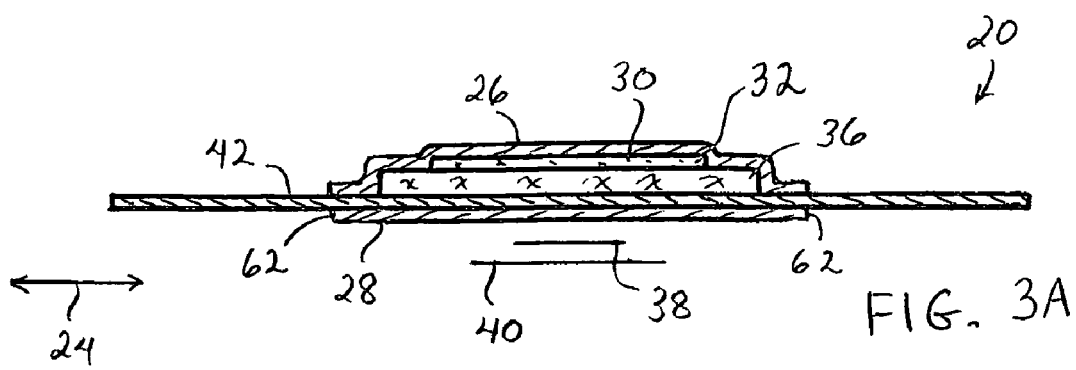
FIG. 3A shows a partially-expanded view of a representative lateral, transverse cross-section through an article having a singular wing-panel positioned against a bodyside surface of a backsheet of the article.

In desired arrangements, the laterally-opposed side portions 43 of the wing-panel 42 can extend laterally beyond the pair of laterally-opposed, terminal side edges 62 of the backsheet 28. The wing-panel may be joined to a bodyside surface of the backsheet (e.g. FIG. 3A), or may be joined to an outward, garment-side surface of the backsheet (e.g. FIG. 3). Additionally, at least a significant portion of the wing-panel 42 can be arranged to extend along and across an outward, garment-side surface of the absorbent body 30. The wing-panel may also be configured to provide an immediately adjacent contact with at least a portion of the garment-side surface of the absorbent body.

The wing-panel material should be strong enough to process well and not tear or rip while the final article is in ordinary use. The wing-panel material can, for example, have a thickness within the range of about 0.25 mm–3.0 mm, and can exhibit a desired porosity value.

Where the wing-panel is joined to a inward, bodyside surface or an outward, garment-side surface of the backsheet, the wing-panel may be liquid-permeable or may be operatively liquid-impermeable, as desired. Particular configurations can include a breathable nonwoven fabric, a non-breathable nonwoven fabric, a spunbond fabric, a carded web, a thermally bonded web, a breathable film material, a non-breathable film or the like, as well as combinations thereof. Suitable breathable materials can typically have a Water Vapor Transmission Rate (WVTR) of at least a minimum of 700 grams water per square meter of material per 24 hr (g/m²/24 hr) and can have a WVTR of at least about 1200 g/m2/24 hr. WVTR testing is a conventional test that is well known to those skilled in the art of breathable materials. For example, see INDA IST. 70.4-99 "Standard Test Method for Water Vapor Transmission Rate Through Nonwoven and Plastic Film using a Guard Film and Vapor Pressure Sensor", developed by the Association of the Nonwoven Fabrics Industry (formerly the International Nonwovens and Disposables Association). Suitable testing systems are available from commercial vendors, such as Mocon, Inc., a business having offices located in Minneapolis, Minn., U.S.A.

The wing-panel materials can be substantially non-stretchable or may be stretchable. The wing-panel material may also be capable of providing a selected amount of elastomeric stretch and retraction. In particular configurations, the wing-panel material can exhibit a maximum stretch elongation value of up to about 300%, or more. In other configurations, the wing-panel material can exhibit a minimum stretch elongation value of 50%. In other features, the wing-panel material can have a basis weight which is within the range of about 0.5–3 ounces per square yard (about 17–102 g/m²). By employing such wing-panel materials, the wing-panel can provide better fit characteristics, and can help provide improved leak protection.

Figure 3B:
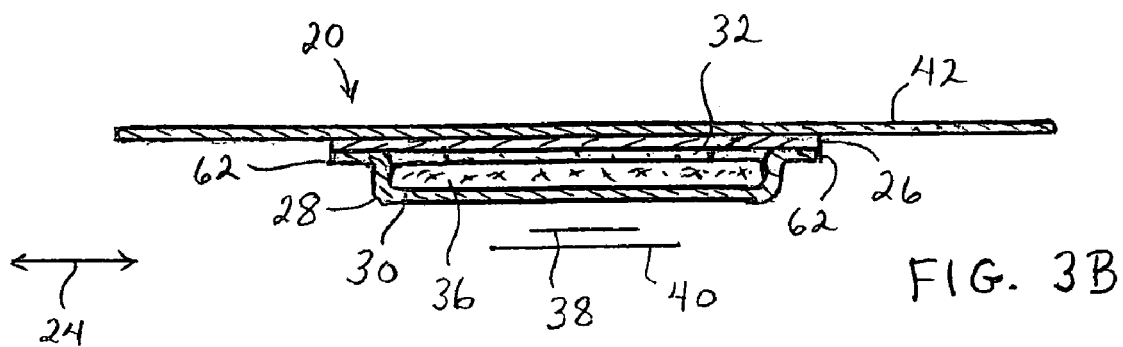
FIG. 3B shows a partially-expanded view of a representative lateral, transverse cross-section through an article having a singular wing-panel positioned against a bodyside surface of a topsheet of the article.
Figure 3C:
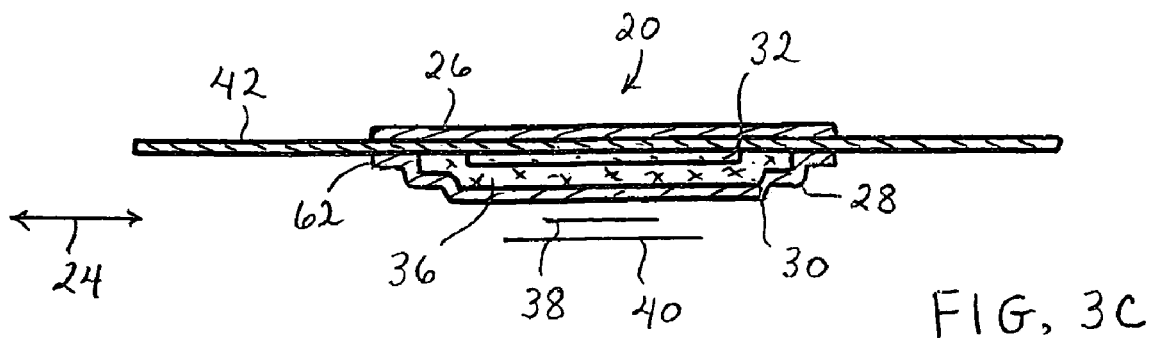
FIG. 3C shows a partially-expanded view of a representative lateral, transverse cross-section through an article having a singular wing-panel positioned against a garment-side surface of a topsheet of the article.

In other configurations, at least an operative portion of the wing-panel 42 can alternatively extend substantially continuously along an entire cross-directional width of a corresponding region of the topsheet 26. As representatively shown, laterally-opposed side portions of the wing-panel 42 can extend laterally beyond the pair of laterally-opposed, terminal side edges of the topsheet 26. The wing-panel 42 can be joined to a major facing-surface of the topsheet 26. More particularly, the wing panel may be operatively joined to a bodyside surface of the topsheet (e.g. FIG. 3B) or to an outward, garment-side surface of the topsheet (e.g. FIG. 3C). The wing-panel 42 can also be arranged to extend along and across an inward, bodyside surface of the absorbent body 30. Additionally, the wing-panel may be configured to provide an immediately adjacent contact with at least a portion of the bodyside surface of the absorbent body.

In still other aspects, the wing-panel 42 can be configured to extend between selected component layers or strata of the absorbent body 30, and in particular arrangements, can be sandwiched between the selected absorbent body components. For example, the wing-panel 42 can be located and interposed between the intake layer 32 and the retention layer 36 of the absorbent body 30. Where the wing-panel 42 is provided by a singular component, an operative medial portion of the wing-panel 42 can extend substantially continuously along the entire cross-directional width of a corresponding region of the absorbent body. In particular, the wing-panel can extend substantially continuously along the entire cross-directional widths of corresponding regions of the intake layer 32 and retention layer 36.

Where the wing-panel is positioned to extend adjacent the topsheet or between selected components of the absorbent body 30, the wing-panel can be composed of a liquid-permeable material. Additionally, the material may be configured to provide improved intake, distribution and/or retention of liquid, thereby providing additional absorbency benefits.

Figure 5:
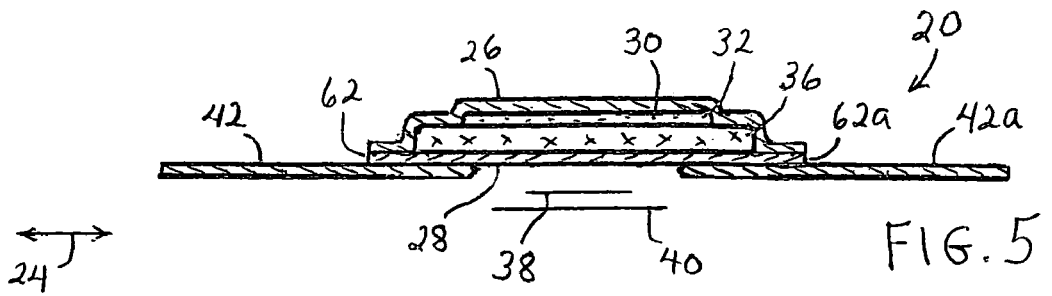
FIG. 5 shows a partially-expanded view of a representative lateral, transverse cross-section through an article having a plurality of wing-panels positioned against a garment-side surface of a backsheet of the article.
Figure 5A:
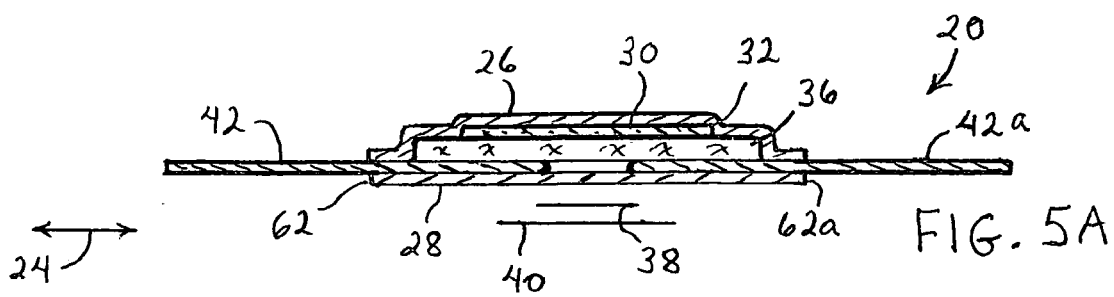
FIG. 5A shows a partially-expanded view of a representative lateral, transverse cross-section through an article having a plurality of wing-panels positioned against a bodyside surface of a backsheet of the article.
Figure 5B:
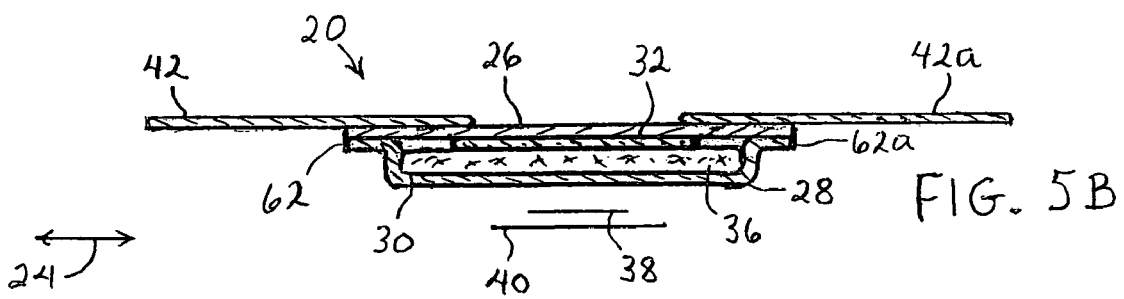
FIG. 5B shows a partially-expanded view of a representative lateral, transverse cross-section through an article having a plurality of wing-panels positioned against a bodyside surface of a topsheet of the article.
Figure 5C:
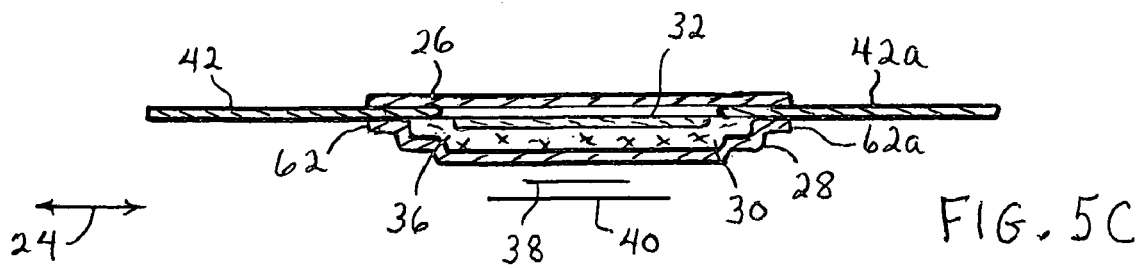
FIG. 5C shows a partially-expanded view of a representative lateral, transverse cross-section through an article having a plurality of wing-panels positioned against a garment-side surface of a topsheet of the article.

With reference to FIGS. 4 through 5C, the article 20 can alternatively include at least one cooperating pair of wing-panel members 42, 42a. Desirably, each pair of wing-panel members can be operatively, laterally aligned with each other along the transverse cross-direction 24. The pair of wing-panel members 42, 42a can be substantially mirror-images of each other. Additionally, the terminal, inboard edges of each cooperating pair of wing-panel members can be laterally spaced-apart by a discrete distance. With respect to each cooperating pair of wing-panels, a first, separately provided wing-panel component or member has a construction and configuration that can be arranged to extend laterally outward from a first laterally-terminal side edge of the topsheet 26 and/or backsheet 28. For example, a desired construction of the first wing-panel can be configured to extend laterally outward from a first laterally-terminal side edge 62 of the backsheet 28. A second, separately provided wing-panel component or member 42a can extend laterally outward from a second laterally-terminal side edge of the topsheet 26 and/or backsheet 28. For example, a desired construction of the second wing-panel can be configured to extend laterally outward from a second laterally-terminal side edge 62a of the backsheet 28.

A contoured side-edge 64, 64a of each individual wing-panel section 42, 42a, respectively, can provide a substantially continuous extension from a corresponding contoured side-edge of the topsheet 26 and/or backsheet 28. For example, the contoured side-edge 64, 64a of each wing-panel section 42, 42a, respectively, can provide a substantially continuous extension from a corresponding contoured side-edge 62, 62a of the backsheet 28. The outboard wing-section 43, 43a of its corresponding wing-panel 42, 42a, respectively, can extend beyond its corresponding, laterally-opposed side-edge of the topsheet 26 and/or backsheet 28 along the wing-section distance 68. Accordingly, a laterally-opposed pair of wing-sections 43, 43a can be configured to extend laterally outboard from the laterally-opposed side edges of the topsheet and/or backsheet. In a particular arrangement, a cooperating, laterally-opposed pair of wing-panels 42, 42a can extend beyond their corresponding, laterally-opposed side-edges 62, 62a, respectively, of the backsheet 28, and each individual wing-panel can extend over the desired wing-section distance 68.

With reference to FIGS. 5 through 5C, each of the individual wing-panel members 42, 42a can be operatively joined and attached to the article 20 in accordance with the various configurations pertaining to the singular wing-panel that are disclosed herein. For example, either or both of the wing-panel members 42, 42a can be joined to a garment-side or bodyside surface of the backsheet 28, and/or a garment-side or bodyside surface of the topsheet 26, as desired. In the various configurations of the article, any or all of the wing-panels can be operatively attached to the article 20 with hotmelt adhesive. It should be readily appreciated, however, that any other operative adhesive or attachment mechanism may alternatively be employed. Such mechanisms can include thermal bonds, ultrasonic bonds, stitches, pins, staples, rivets or the like, as well as combinations thereof.

In another feature of the invention, each wing-panel 42, or any desired combination of the employed wing-panels, can include a panel-fastener component 44 which is operatively joined to an appointed engagement surface of the associated wing-panel. The panel-fastener 44 can include any operative fastener component, such as a component of an interengaging mechanical faster, an adhesive fastener, a cohesive fastener, a magnetic fastener, an electromechanical fastener or the like, as well as combinations thereof.

With reference to FIGS. 1–1A, FIGS. 2–2A and FIGS. 4–4A, for example, each panel-fastener 44 can include a hook or other "male" component of an interengaging mechanical fastener system. Any operative hook component may be employed. For example, a suitable hook component materials can include a J-hook, mushroom-head hook, flat-top nail-head hook, a palm-tree hook, a multiple-J hook or the like, as well as combinations thereof.

An operative first section of the selected hook component can be joined to a major facing surface of at least a first wing-panel portion 42, and can be configured to contact or otherwise engage a cooperating, second wing-panel portion during ordinary use. Additionally, an operative second section of a hook component, composed of the same or different type of hook material, can be joined to a major facing surface of the second wing-panel portion, and can be configured to contact or otherwise engage an outward surface of the wearer's undergarment during ordinary use. For example, the hook component can be arranged to operatively engage and removably attach to the outward surface of a crotch region of the undergarment.

Each wing-panel 42, or any desired combination of the employed wing-panels, can include a cooperating, second fastener-component. For example, the second fastener-component can be a loop or other "female" component 78 of an interengaging mechanical fastener system. Any operative loop component may be employed. For example, a suitable loop component material can include a woven fabric, a knit fabric, a nonwoven fabric, a fabric laminated to a substrate or the like, as well as combinations thereof.

An operative first section of a selected loop component 78 can be joined to a major facing surface of at least the second wing-panel portion, and can be configured to contact or otherwise engage the hook component on the first wing-panel portion 42 during ordinary use. Additionally, an operative second section of a loop component, composed of the same or different type of loop material, can be joined to a major facing surface of the first wing-panel portion 42. As a result, the user can have the option of alternatively attaching the second hook component of the second wing-panel onto the second loop component of the first wing-panel. Accordingly, the first hook component may alternatively be engaged with the outward surface of the wearer's undergarment.

Each or any desired combination of the provided loop components may be a separately provided member that is subsequently joined and assembled to its corresponding wing-panel portion 42. In a desired feature, each or any desired combination of the provided loop components can be integrally provided by the material employed to construct its corresponding wing-panel portion.

In the various arrangements of the present invention, the hook component can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

If the hook concentration density is outside the desired values, the engagement force between the hook and loop materials can be too low, and can allow the wing-panel wings to undesirably unfasten during ordinary use.

Examples of suitable hook materials can include 85-Series and 61-Series hook materials available from Velcro, U.S.A., a business having offices located in Manchester, N.H., U.S.A. The hook materials can, for example, have a hook density of about 775 hooks/cm$^2$.

In a particular aspect, the material of the loop component may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996; the entire disclosure of which is incorporated herein by reference in a manner that is consistent herewith.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Figure 6:
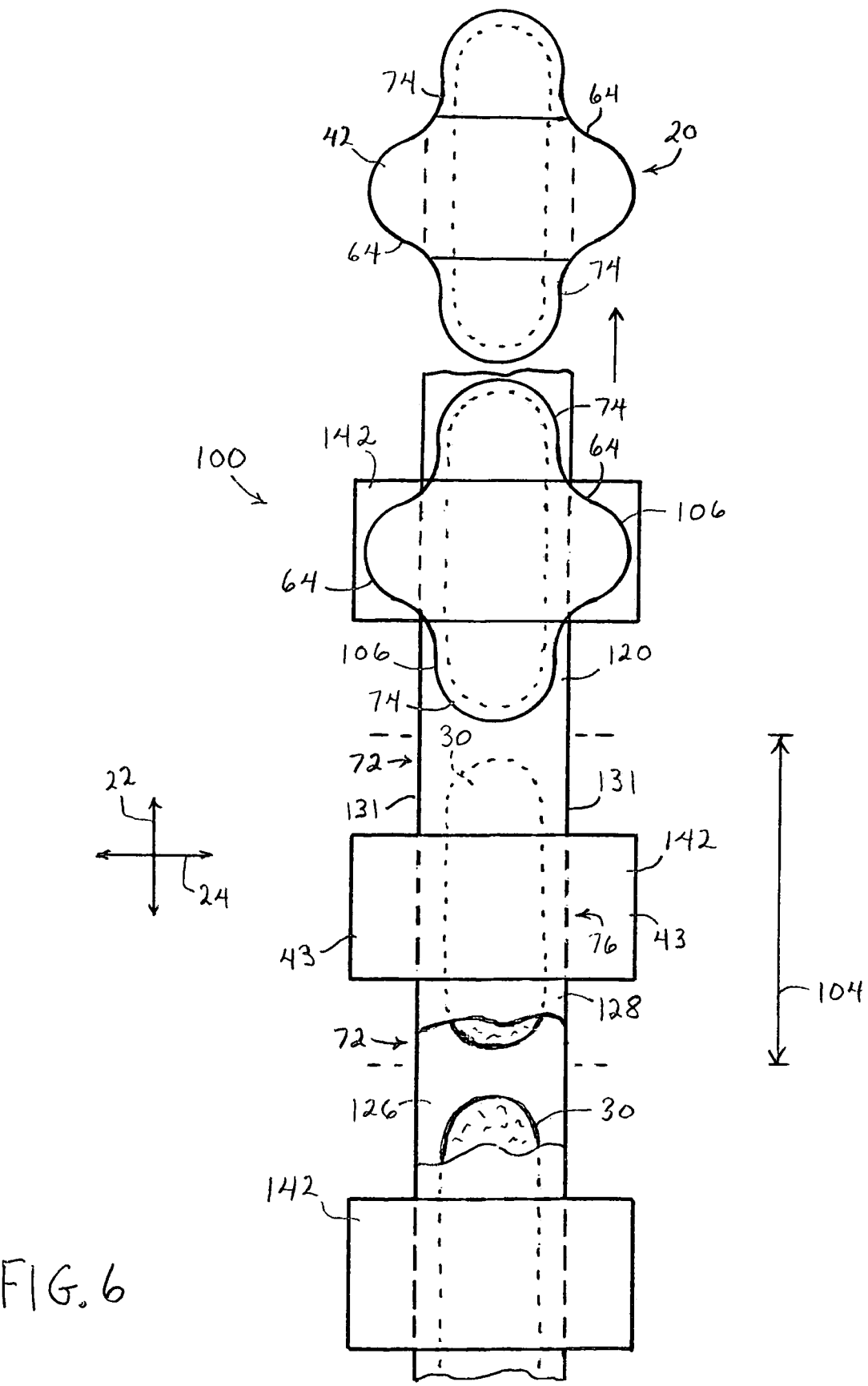
FIG. 6 shows a partially cut-away, schematic, top view of a representative apparatus and process for placing at least one wing-panel on an article web, and subsequently cutting the wing-panel and article web wherein a singular wing-panel has a portion that traverses an entire width of an outside surface of the article web.
Figure 7:
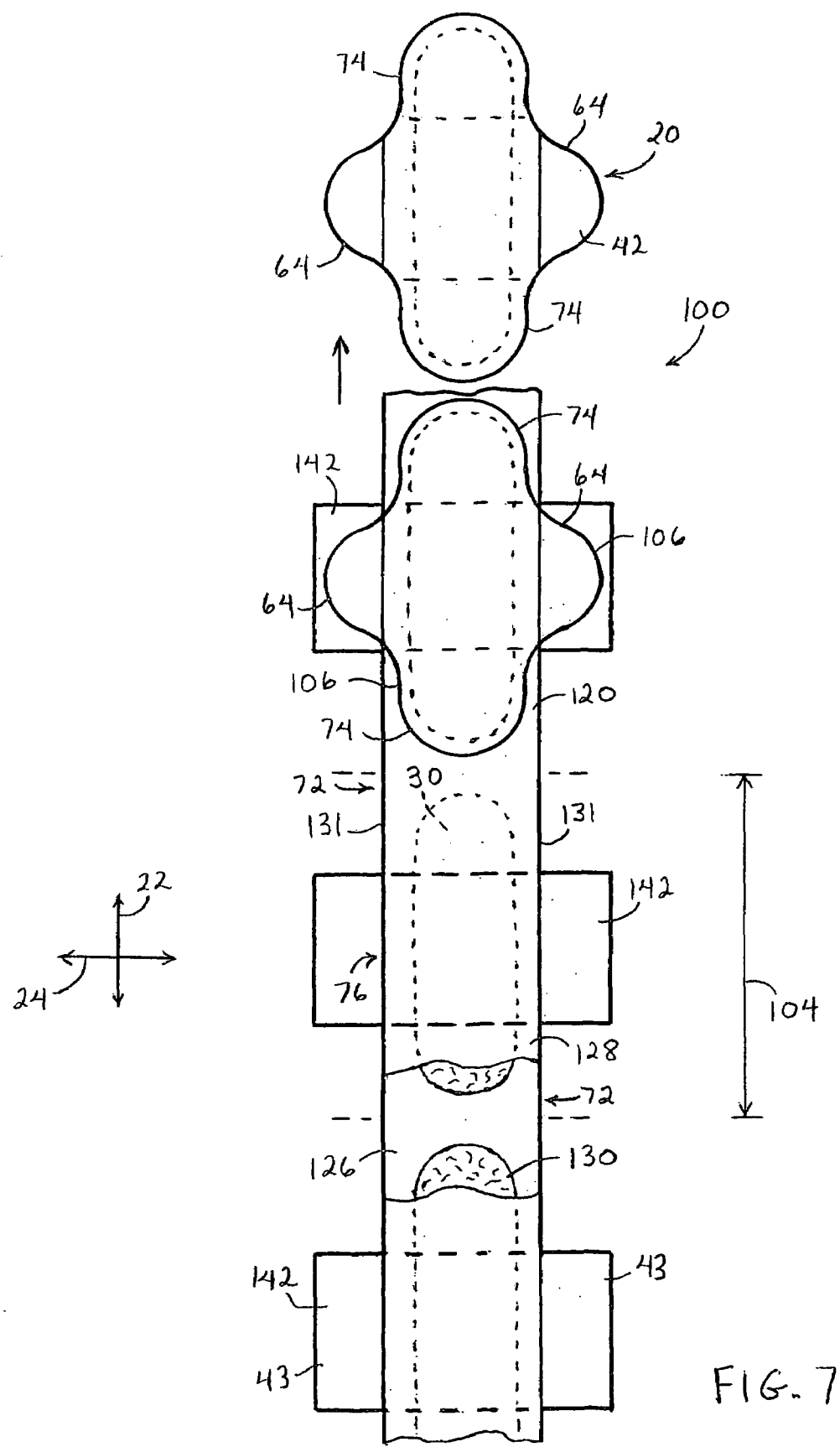
FIG. 7 shows a partially cut-away, schematic top view of another representative apparatus and process for placing at least one wing-panel on an article web, and subsequently cutting the wing-panel and article web, wherein a singular wing-panel has a portion that traverses an entire width of an inner surface of the article web.
Figure 8:
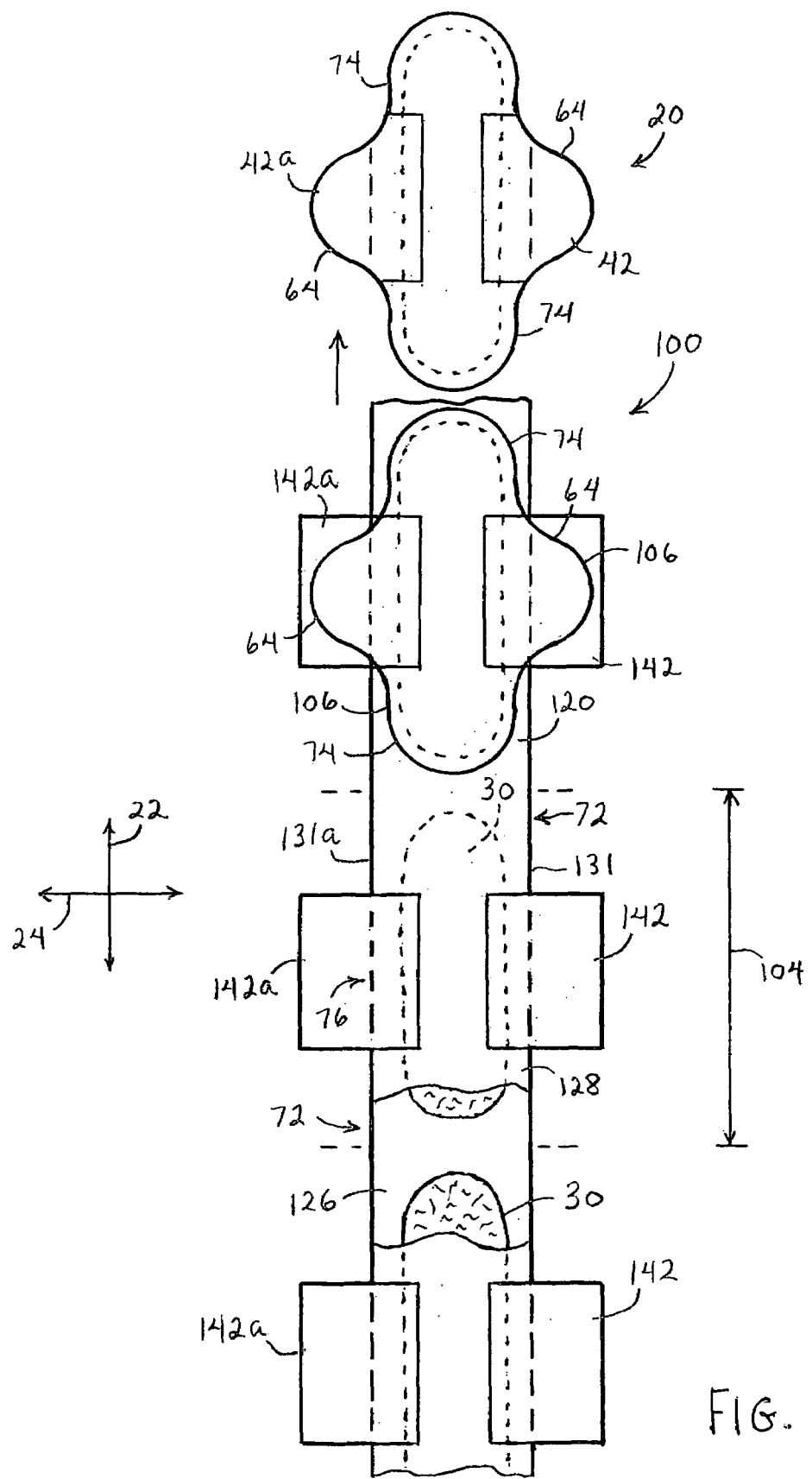
FIG. 8 shows a schematic, top view of a representative apparatus and process for placing a plurality of cooperating pairs of wing-panels on an article web, and subsequently cutting the wing-panels and article web, wherein laterally-opposed pairs of wing-panels traverse only a portion of the width of an outside surface of the article web.

With reference to FIGS. 6, 7 and 8, a process 100 for forming the article 20 includes delivering an article web 120 which has a longitudinal-direction 22 and a lateral cross-direction 24, and provides an interconnected plurality of article-segments 104. Each article-segment has included an intermediate portion 76 located between a pair of longitudinally-opposed end portions 72. In a particular aspect, at least one selected article-segment 104 can include at least one wing-panel component or member 142, which has been operatively joined to its corresponding, selected article-segment 104 and configured to extend beyond at least one laterally-opposed side edge of said article web 120 in the intermediate portion 76 of the corresponding article-segment 104. Desirably, each of the wing-panel members 142 can be a separately provided component. In another feature, the process 100 can also include a substantially continuous severing of the article web 120 and the at least one wing-panel member 142 to provide a contoured composite web. In a particular feature, the contoured composite web can include at least one contoured wing-panel 142. With respect to the selected article-segment 104, a contoured side-edge 64 of the resulting, contoured wing-panel 142 can be configured to extend substantially continuously from a cooperatively contoured side-edge 74 of said article web. Desirably, the contoured wing-panel 142 can be configured and arranged to be operatively wrapped about a side edge of a wearer's undergarment.

By incorporating its various aspects, features and configurations alone or in desired combinations, the method of the invention can provide an improved article having the attractiveness and aesthetic appeal afforded by integrally formed wing portions, while also providing the versatility and enhanced performance that can arise from incorporating separately provided wing portions that are constructed from different materials having selected characteristics and performance parameters. The method can more efficiently produce desired articles at high speed and with a reduced cost of materials.

In particular aspects, the process 100 can include a configuring of the article web 120 to include a backsheet web 128. Accordingly, each article-segment 104 can include a corresponding portion of a backsheet web 128. The article web may also be configured to include a topsheet web 126. Accordingly, the process may further include a configuring of each article-segment 104 to include a corresponding portion of the topsheet web 126. Additionally, the article web can be configured to include one or more absorbent bodies 30, and the absorbent bodies can be sandwiched between the backsheet web and topsheet web at intermittent locations along the longitudinal-direction 22 of the article web. Accordingly, each article-segment 104 can be configured to include an individual absorbent body 30 which is sandwiched between its corresponding portion of the topsheet web 126 and its corresponding portion of the backsheet web 128.

The article web 120 can be transported or otherwise moved through the process at a selected delivery speed. In a particular aspect of the invention, the delivery speed can be at least a minimum of about 50 ft/min (about 15.2 m/min). The delivery speed can alternatively be at least about 100 ft/min (about 30.5 m/min), and can optionally be at least about 500 ft/min (about 152.4 m/min) to provide improved performance. In other aspects, the delivery speed can be up to a maximum of about 2000 ft/min (about 610 m/min), or more. The delivery speed can alternatively be up to about 1500 ft/min (about 457 m/min), and can optionally be up to about 1000 ft/min (about 305 m/min) to provide improved performance and manufacturing efficiencies.

As representatively shown, a plurality of wing-panel members 142 can be joined to the article web 120 at intermittent spaced-apart locations along a longitudinal-direction 22 of the article web 120 to form a desired composite assembly. Each wing-panel member can desirably be joined with the article web in a layered arrangement. Additionally each wing-panel 142 can be operatively joined with a configuration that can be operatively arranged to extend laterally outboard from the article web at its appointed article-segment 104. Desirably, the wing-panel members can be regularly spaced-apart at substantially equal intervals and spacing distances along the longitudinal-direction of the article web, but may optionally be irregularly spaced-apart along the longitudinal-direction of the article web.

Any operative mechanism or technique may be employed to provide the wing-panel members 142 and to position and secure the wing-panel members on the article web 120. Suitable devices can, for example, include vacuum-slip rolls, end cut modules, transfer rolls or the like, as well as combinations thereof. Conventional devices and associated control systems are well known, and can be obtained from commercial vendors.

The various arrangements of the process can be configured to operatively join the wing-panel or wing-panels to the selected article-segment in arrangements that are substantially in accordance with the various constructions and configurations of the individual articles 20 that are set forth in the present disclosure. Accordingly, the process can be arranged to produce an individual article-segment 104 or a selected plurality of article-segments having the configurations and features which are incorporated into any of the various constructions of the individual articles 20 that are disclosed herein.

In the various configurations of the process, a plurality of wing-panel members 142 can be joined to the backsheet web 128 at intermittent spaced-apart locations along the longitudinal-direction 22 of the article web 120 to form the desired composite. Each wing-panel 142 can be connected and secured to the backsheet web 128 in any operative arrangement. In a particular configuration, the wing-panel can be operatively joined to an appointed garment-side of the backsheet web 128 at an appointed article-segment 104. Optionally, the wing-panel can be operatively joined to an appointed bodyside of the backsheet web 128.

With reference to FIGS. 6 and 7, for example, particular configurations of the process can operatively join and attach a plurality of wing-panel members 142 wherein each wing-panel member is a singular, individual wing-panel member. The singular wing-panel has a contiguous unitary structure, and may be provided by a composite structure having one or more constituent elements. At least an operative portion or section of the individual, singular wing-panel member 142 can extend substantially continuously along an entire cross-directional width of a corresponding portion of the article web that is present in the corresponding article-segment 104. As representatively shown, for example, a selected medial section of the wing-panel 142 may be configured to extend substantially continuously along the entire cross-directional width of the corresponding article-segment that has been provided by the associated article web portion. Additionally, a pair of distal side sections of the singular, individual wing-panel can be configured to extend laterally beyond a pair of laterally-opposed, terminal side edges of the article web 120 at the corresponding article-segment 104. As representatively shown, at least a pair of distal side sections 43 of the singular wing-panel member 142 can be constructed and arranged to extend laterally beyond a corresponding pair of laterally-opposed, terminal side edges of the article web. In particular arrangements, an operative portion or section of the individual wing-panel can extend substantially continuously along an entire cross-directional width of a corresponding portion of the backsheet web 128 that is present in the corresponding article-segment 104. Additionally, distal side sections of the singular, individual wing-panel can also extend laterally beyond the pair of laterally-opposed, terminal side edges 131 of the of the backsheet web 128, and the singular wing-panel can be joined to the intermediate portion 76 of its corresponding article-segment.

With reference to FIG. 8, another configuration of the process can operatively join and attach a first plurality of separately provided wing-panel component members 142 to the article web 120 at spaced-apart locations along a first side edge 131 of the article web in the longitudinal-direction 22. Additionally, the process can be configured to operatively join and attach a second plurality of separately provided web-panel component members 142a which are spaced-apart in the longitudinal-direction 22 and positioned at cooperating locations along a laterally-opposed second side-edge 131a of the article web 120. As representatively shown, a cooperating pair of wing panel members 142 and 142a can be positioned at substantially mirror-image locations along the article web 120, and the opposed wing-panel members can be joined to the intermediate portion 76 of their corresponding article-segment.

A desired arrangement of the process can, for example, operatively join and attach the first plurality of wing-panel members 142 to the article web 120 at spaced-apart locations which are positioned along a first side edge 131 of the backsheet web 128 in the longitudinal-direction 22. Additionally, the process can operatively join and attach the second plurality of separately provided web-panel components 142a at cooperating locations which are spaced-apart in the longitudinal-direction and positioned along a second side-edge 131a of the backsheet web 128.

The substantially continuous severing of the article web 120 and the at least one wing-panel 142 to provide the contoured composite web can be provided by any conventional cutting or severing mechanism or technique. For example, the cutting or severing mechanism or technique may include a die-cutter, a rotary knife, a water-cutter, a laser cutter, an electron beam or other energy beam cutter or the like, as well as combinations thereof. Suitable devices and equipment, with associated operating and control systems, are well known and are available from commercial vendors.

The severing of the article web 120 and the wing-panel member 142 can be configured to extend along at least one composite transition section in which a portion of the wing-panel member has been substantially simultaneously severed along with a corresponding portion of the article web that has been joined with the wing-panel member. As representatively shown, the corresponding portion of the article web can be arranged in a laminated or otherwise layered configuration with respect to its associated portion of the wing-panel member. In a particular aspect, the composite transition section can be arcuate or otherwise nonlinear. In another aspect the transition section and can extend continuously with no abrupt angular breaks. Where the article web 120 includes the backsheet web 128, the severing of the article web and the wing-panel member along the composite transition section can be configured to sever a portion of the backsheet web. Where the article web 120 includes the backsheet web 128 and topsheet web 126, the severing of the article web and the wing-panel member along the composite transition section can be configured to sever a corresponding portion of the backsheet web and a corresponding portion of the topsheet web.

In desired configurations, the severing of the article web and the wing-panel member can be configured to extend along a plurality of composite transition sections. Each composite transition section can include a portion of the wing-panel member which has been substantially simultaneously severed with a corresponding portion of the joined article web. Additionally, the severing of the article web and the wing-panel member can provide one or more arcuate composite transition sections that are configured to be concave outward.

As representatively shown, the various configurations of the process can further include a dividing of the article web 120 along appointed separation lines 106 in correspondence with the appointed article-segments 104 to provide a plurality of the desired individual articles 20, such as the representatively shown feminine care or other personal care article. In a particular feature, the severing of the article web and wing panel can be operatively coordinated and combined with the dividing of the article web into the individual articles 20. It should be readily appreciated that any conventional separating or dividing mechanism or technique may be employed. For example, the separating or dividing mechanism or technique may include a die-cutter, a rotary knife, a water-cutter, a laser cutter, an electron beam or other energy beam cutter or the like, as well as combinations thereof. Suitable devices and equipment (and associated operating and control systems) are well known and are available from commercial vendors.

It should be readily apparent that an individual article-segment 104 can be constructed and arranged to substantially correspond to an individual finished article 20. As a result, the corresponding portion of the backsheet web 128 can provide the backsheet 28 of the article 20, and the corresponding portion of the topsheet web 126 can provide the topsheet 26 of the article. Additionally, the corresponding wing-panel member or members 142 can provide the contoured wing-panel or wing-panels 42 of the article. It should also be readily appreciated that the process of the invention can be appropriately constructed and arranged to operatively produce any of the aspects, features and configurations which pertain to the article 20 disclosed herein.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A process for forming an article, said process comprising delivering an article web which has a longitudinal-direction and a lateral cross-direction, and provides an interconnected plurality of article-segments, each article-segment including an intermediate portion located between a pair of longitudinally-opposed end portions, at least one article-segment having included at least one separately provided singular, individual wing-panel member, the singular wing-panel member operatively joined to its corresponding article-segment and configured to extend beyond a pair of laterally-opposed, terminal side edge of said article web in the intermediate portion of its corresponding article-segment; and substantially continuously severing said article web and said wing-panel member to provide a contoured composite web having a contoured wing-panel, wherein a contoured side-edge of said contoured wing-panel extends substantially continuously from a cooperatively contoured side-edge of said article web, the contoured wing-panel configured to be wrapped about a side edge of a wearer's undergarment;

wherein a plurality of the singular, individual wing-panel members have been joined to said article web at intermittent, space-apart locations along a longitudinal-direction of said article web;

at least an operative portion or section of each singular, individual wing-panel member extends substantially continuously along an entire cross-directional width of its corresponding article-segment.

2. A process as recited in claim 1, wherein said article web has included a backsheet web; a liquid-permeable topsheet web and a plurality of absorbent bodies;

each article-segment has included a corresponding portion of the backsheet web; a corresponding portion of the topsheet web, and at least one corresponding absorbent body that has been sandwiched between the portion of said topsheet web and the portion of said backsheet web; and each singular, individual wing-panel member has been operatively joined to its corresponding article-segment on a bodyside of the backsheet web, and has been arranged to extend along a garment-side surface of its corresponding absorbent body.

3. A process as recited in claim 2, further including a dividing of said article web to provide a plurality of individual, personal care articles.

4. A process as recited in claim 2, wherein the severing of the article web and the wing-panel member has been configured to extend along a composite transition section in which a portion of the wing-panel member has been substantially simultaneously severed with a portion of the article web that has been joined with the wing-panel member.

5. A process as recited in claim 4, wherein the severing of the article web and the wing-panel member along the composite transition section has been configured to sever a backsheet web portion and a topsheet web portion of the article web.

6. A process as recited in claim 4, wherein the severing of the article web and the wing-panel member has bean configured to extend along a plurality of composite transition sections, each composite transition section including a portion of the wing-panel member which has been substantially simultaneously severed with a portion of the article web that has been joined with the wing-panel member.

7. A process as recited in claim 4, wherein the severing of the article web and the wing-panel member configures the composite transition section to be arcuate and concave outward.

8. A process as recited in claim 1, wherein said article web has included a backsheet web; a liquid-permeable topsheet web and a plurality of absorbent bodies;

each article-segment has included a corresponding portion of the backsheet web; a corresponding portion of the topsheet web, and at least one corresponding absorbent body that has been sandwiched between the portion of said topsheet web and the portion of said backsheet web; and each singular, individual wing-panel member has been operatively joined to its corresponding article-segment on a bodyside of the topsheet web.

9. A process as recited in claim 8, further including a dividing of said article web to provide a plurality of individual, personal care articles.

10. A process as recited in claim 8, wherein the severing of the article web and the wing-panel member has been configured to extend along composite transition section in which a portion of the wing-panel member has been substantially simultaneously severed with a portion of the article web that has been joined with the wing-panel member.

11. A process as recited in claim 10, wherein the severing of the article web and the wing-panel member along the composite transition section has been configured to sever a backsheet web portion of the article web.

12. A process as recited in claim 10, wherein the severing of the article web and the wing-panel member has been configured to extend along a plurality of composite transition sections, each composite transition section including a portion of the wing-panel member which has been substantially simultaneously severed with a portion of the article web that has been joined with the wing-panel member.

13. A process as recited in claim 10, wherein the severing of the article web and the wing-panel member configures the composite transition section to be arcuate and concave outward.

14. A process as recited in claim 1, wherein
said article web has included a backsheet web; a liquid-permeable topsheet web and a plurality of absorbent bodies;
each article-segment has included a corresponding portion of the backsheet web; a corresponding portion of the topsheet web, and at least one corresponding absorbent body that has been sandwiched between the portion of said topsheet web and the portion of said backsheet web; and
each singular, individual wing-panel member has been operatively joined to its corresponding article-segment on a garment-side of the topsheet web.

15. A process as recited in claim 14, further including a dividing of said article web to provide a plurality of individual, personal care articles.

16. A process as recited in claim 14, wherein the severing of the article web and the wing-panel member has been configured to extend along composite transition section in which a portion of the wing-panel member has been substantially simultaneously severed with a portion of the article web that has been joined with the wing-panel member.

17. A process as recited in claim 16, wherein the severing of the article web and the wing-panel member along the composite transition section has been configured to sever a backsheet web portion and a topsheet web portion of the article web.

18. A process as recited in claim 16, wherein the severing of the article web and the wing-panel member has been configured to extend along a plurality of composite transition sections, each composite transition section including a portion of the wing-panel member which has been substantially simultaneously severed with a portion of the article web that has been joined with the wing-panel member.

19. A process as recited in claim 16, wherein the severing of the article web and the wing-panel member configures the composite transition section to be arcuate and concave outward.

20. A process as recited in claim 1, wherein
said article web has included a backsheet web; a liquid-permeable topsheet web and a plurality of absorbent bodies;
each article-segment has included a corresponding portion of the backsheet web; a corresponding portion of the topsheet web, and at least one corresponding absorbent body that has been sandwiched between the portion of said topsheet web and the portion of said backsheet web;
each absorbent body includes component layers; and
each singular, individual wing-panel member has been operatively joined to its corresponding article-segment, and has been sandwiched between component layers of the absorbent body that corresponds to the article-segment.

* * * * *